(12) United States Patent
Ciccone et al.

(10) Patent No.: US 8,628,537 B2
(45) Date of Patent: *Jan. 14, 2014

(54) ADJUSTABLE TOOL FOR CANNULATED FASTENERS

(75) Inventors: Paul Ciccone, Lincoln University, PA (US); Michael Mazzio, Schwenksville, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 988 days.

This patent is subject to a terminal disclaimer.

(21) Appl. No.: 12/576,366

(22) Filed: Oct. 9, 2009

(65) Prior Publication Data

US 2010/0030282 A1 Feb. 4, 2010

Related U.S. Application Data

(62) Division of application No. 10/820,080, filed on Apr. 6, 2004, now Pat. No. 7,604,643.

(51) Int. Cl.
*A61B 17/60* (2006.01)
*A61F 2/00* (2006.01)

(52) U.S. Cl.
USPC ........................................................ 606/104

(58) Field of Classification Search
USPC ............. 606/280, 286, 297, 99, 104; 81/439, 81/442, 445; 7/158, 165
See application file for complete search history.

(56) References Cited

U.S. PATENT DOCUMENTS

| | | |
|---|---|---|
| 126,366 A | 4/1872 | Wills |
| 848,194 A | 3/1907 | McMurtry |
| 851,181 A | 4/1907 | McMurtry |
| 868,436 A | 10/1907 | Hermand |
| 1,474,236 A | 11/1923 | Byrne |
| 1,503,692 A | 8/1924 | McCarthy |
| 1,537,929 A | 5/1925 | Lee |
| 1,543,175 A | 6/1925 | McCarthy |
| 2,247,500 A | 7/1941 | Hutchinson, Jr. |
| 2,256,012 A | 9/1941 | Blair |
| 2,277,945 A | 3/1942 | Ashleman |
| 2,366,448 A | 1/1945 | Greene et al. |
| 2,493,398 A | 1/1950 | Fricke |
| 2,506,835 A | 5/1950 | Johnson |
| 2,575,525 A | 11/1951 | Mitchell |
| 2,605,666 A | 8/1952 | Jorgensen et al. |
| 2,611,289 A | 9/1952 | Frank |

(Continued)

FOREIGN PATENT DOCUMENTS

| | | |
|---|---|---|
| DE | 3434807 A1 | 12/1985 |
| EP | 0674880 A1 | 10/1995 |

(Continued)

*Primary Examiner* — Anu Ramana
(74) *Attorney, Agent, or Firm* — Woodcock Washburn LLP

(57) ABSTRACT

A tool is disclosed for use in forming holes in bone and for driving a cannulated fastener into the formed hole. The tool may having a cutting tip for drilling a hole into bone, and may have a shaft and sleeve for accepting the cannulated fastener and for driving it into the drilled hole. The tool may be adjustable to allow fasteners of different lengths to be accepted, while ensuring that a portion of the cutting tip protrudes beyond the end of the fastener. A multiple-screw tool is also disclosed that allows more than one cannulated fastener at a time to be stacked on the tool, thus speeding the installation process.

40 Claims, 8 Drawing Sheets

(56) References Cited

U.S. PATENT DOCUMENTS

| | | | |
|---|---|---|---|
| 2,616,322 | A | 11/1952 | Spreng |
| 2,659,255 | A | 11/1953 | Bates |
| 2,811,883 | A | 11/1957 | Cleaves |
| 2,820,383 | A | 1/1958 | Red, Jr. |
| 2,857,794 | A | 10/1958 | Red, Jr. |
| 2,868,053 | A | 1/1959 | Jorgensen et al. |
| 2,895,360 | A | 7/1959 | Madsen |
| 2,896,489 | A | 7/1959 | Madsen |
| 2,993,397 | A | 7/1961 | Albertson et al. |
| 3,005,367 | A | 10/1961 | Vose |
| 3,063,316 | A | 11/1962 | Salierno |
| 3,289,290 | A * | 12/1966 | Sandor ............... 29/432 |
| 3,336,611 | A | 8/1967 | Schepp |
| 3,932,904 | A | 1/1976 | Nilsson et al. |
| 3,965,510 | A | 6/1976 | Ernst |
| 4,092,753 | A | 6/1978 | Fuhmann |
| 4,107,800 | A | 8/1978 | Jorgensen |
| 4,244,246 | A | 1/1981 | Gillett |
| 4,320,544 | A * | 3/1982 | Bryant et al. ............ 7/158 |
| 4,507,817 | A | 4/1985 | Staffeld |
| 4,537,185 | A | 8/1985 | Stednitz |
| 4,549,538 | A | 10/1985 | Schadrack, III et al. |
| 4,589,178 | A | 5/1986 | Staffeld |
| 4,760,844 | A | 8/1988 | Kyle |
| 4,878,794 | A | 11/1989 | Potucek |
| 4,884,572 | A | 12/1989 | Bays et al. |
| 4,895,148 | A | 1/1990 | Bays et al. |
| 4,924,865 | A | 5/1990 | Bays et al. |
| 4,927,421 | A | 5/1990 | Goble et al. |
| 4,950,270 | A | 8/1990 | Bowman et al. |
| 4,976,715 | A | 12/1990 | Bays et al. |
| 5,059,206 | A | 10/1991 | Winters |
| 5,098,435 | A | 3/1992 | Stednitz et al. |
| 5,129,901 | A | 7/1992 | Decoste |
| 5,152,764 | A | 10/1992 | Goble |
| 5,211,647 | A | 5/1993 | Schmieding |
| 5,249,489 | A | 10/1993 | Weisman |
| 5,255,485 | A | 10/1993 | Lemke et al. |
| 5,308,203 | A | 5/1994 | McSherry et al. |
| 5,334,204 | A | 8/1994 | Clewett et al. |
| 5,354,299 | A | 10/1994 | Coleman |
| RE34,871 | E | 3/1995 | McGuire et al. |
| 5,403,137 | A | 4/1995 | Grun et al. |
| 5,437,211 | A | 8/1995 | Wolf |
| 5,549,431 | A | 8/1996 | Royle |
| 5,551,321 | A | 9/1996 | Bottiglieri |
| 5,569,252 | A | 10/1996 | Justin et al. |
| 5,590,574 | A | 1/1997 | Lide |
| 5,601,562 | A | 2/1997 | Wolf et al. |
| 5,640,889 | A | 6/1997 | Anderson |
| 5,645,547 | A | 7/1997 | Coleman |
| 5,695,497 | A | 12/1997 | Stahelin |
| 5,730,744 | A | 3/1998 | Justin et al. |
| 5,735,854 | A | 4/1998 | Caron et al. |
| 5,741,268 | A | 4/1998 | Schutz |
| 5,833,415 | A | 11/1998 | McSherry |
| 5,868,749 | A | 2/1999 | Reed |
| 5,899,906 | A | 5/1999 | Schenk |
| 5,904,685 | A | 5/1999 | Walawalkar |
| 5,968,045 | A | 10/1999 | Frazier |
| 5,968,046 | A | 10/1999 | Castleman |
| 5,997,541 | A | 12/1999 | Schenk |
| 6,004,321 | A | 12/1999 | Graser |
| 6,030,162 | A | 2/2000 | Huebner |
| 6,048,344 | A | 4/2000 | Schenk |
| 6,096,060 | A | 8/2000 | Fitts et al. |
| 6,164,170 | A * | 12/2000 | Habermehl et al. ............ 81/434 |
| 6,165,203 | A | 12/2000 | Krebs |
| 6,179,840 | B1 | 1/2001 | Bowman |
| 6,273,890 | B1 | 8/2001 | Frazier |
| 6,283,973 | B1 | 9/2001 | Hubbard et al. |
| 6,306,140 | B1 | 10/2001 | Siddiqui |
| 6,328,746 | B1 | 12/2001 | Gambale |
| 6,364,884 | B1 | 4/2002 | Bowman et al. |
| 6,402,757 | B1 | 6/2002 | Moore, III et al. |
| 6,402,766 | B2 | 6/2002 | Bowman et al. |
| 6,423,073 | B2 | 7/2002 | Bowman |
| 6,436,100 | B1 | 8/2002 | Berger |
| 6,436,110 | B2 | 8/2002 | Bowman et al. |
| 6,447,517 | B1 | 9/2002 | Bowman |
| 6,468,277 | B1 | 10/2002 | Justin et al. |
| 6,471,706 | B1 | 10/2002 | Schumacher et al. |
| 6,497,707 | B1 | 12/2002 | Bowman et al. |
| 6,527,777 | B2 | 3/2003 | Justin |
| 6,544,281 | B2 | 4/2003 | ElAttrache et al. |
| 6,554,852 | B1 | 4/2003 | Oberlander |
| 6,557,727 | B1 | 5/2003 | Robertson |
| 6,616,665 | B2 | 9/2003 | Grafton et al. |
| 6,623,486 | B1 * | 9/2003 | Weaver et al. ............... 606/281 |
| 6,629,977 | B1 | 10/2003 | Wolf |
| 6,634,261 | B1 | 10/2003 | Griffin |
| 2001/0027322 | A1 | 10/2001 | Bowman |
| 2001/0037113 | A1 | 11/2001 | Justin |
| 2002/0013608 | A1 | 1/2002 | ElAttrache et al. |
| 2002/0052628 | A1 | 5/2002 | Bowman |
| 2002/0169453 | A1 | 11/2002 | Berger |
| 2002/0183751 | A1 | 12/2002 | Justin et al. |
| 2003/0028193 | A1 | 2/2003 | Weil et al. |
| 2003/0078585 | A1 | 4/2003 | Johnson et al. |
| 2003/0120277 | A1 | 6/2003 | Berger |
| 2003/0125749 | A1 | 7/2003 | Yuan et al. |
| 2003/0125750 | A1 | 7/2003 | Zwimmann et al. |

FOREIGN PATENT DOCUMENTS

| | | |
|---|---|---|
| EP | 0674880 B1 | 12/1996 |
| JP | 5060119 A | 3/1993 |
| JP | 8071083 A | 3/1996 |

* cited by examiner

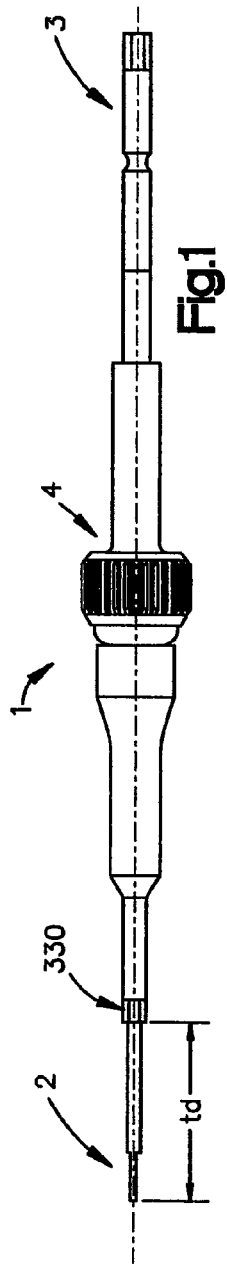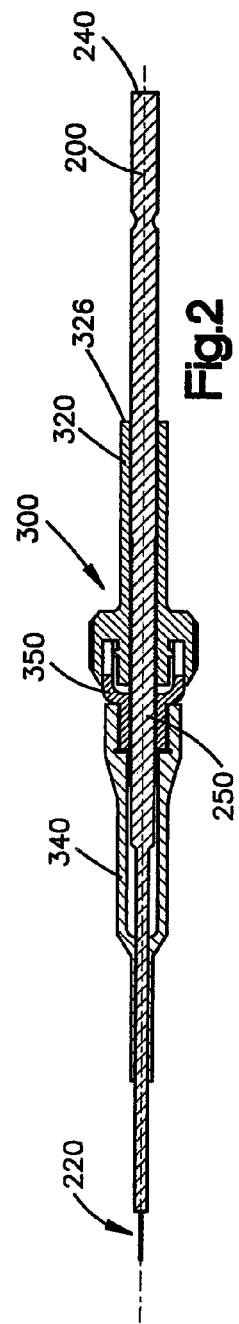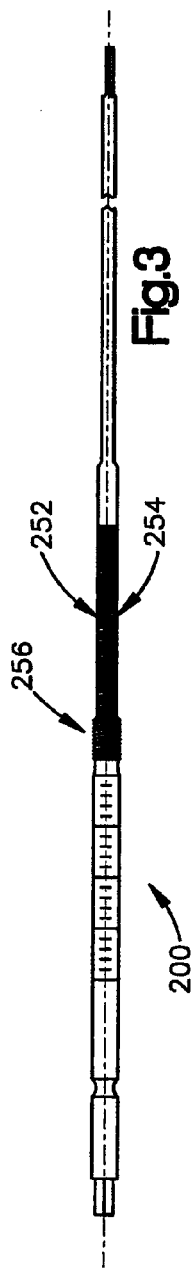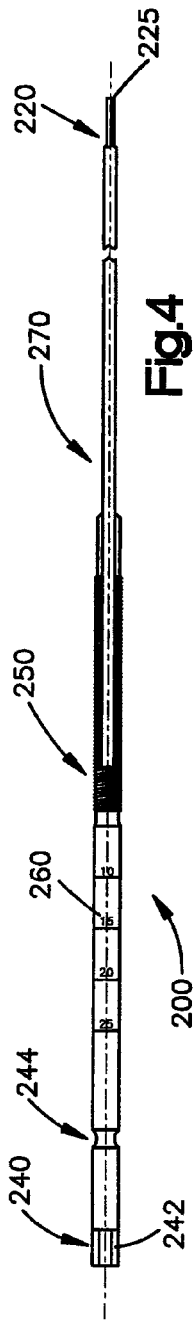

ADJUSTABLE TOOL FOR CANNULATED FASTENERS

CROSS REFERENCE TO RELATED APPLICATION

This application is a Divisional Application of U.S. patent application Ser. No. 10/820,080, filed Apr. 6, 2004, the disclosure of which is incorporated herein by reference in its entirety.

TECHNICAL FIELD

The present invention is directed to a tool for drilling holes in bone and driving cannulated fasteners into the drilled holes. The tool has an adjustable feature that allows it to be used with cannulated fasteners of various lengths. The tool may have a blade for drilling a fastener hole in advance of the screw and may also be used to rotate the fastener to insert it into bone. The tool is provided with a cutting blade and a polygonal section matching the shape of at least a portion of the cannulation of the screw to allow the screw to be rotated using the tool.

BACKGROUND

The present invention relates generally to a cannulated screw system for use in orthopedic surgery. Bone screws are generally installed after a screw hole has been separately drilled. As such, current systems generally require separate hole drilling and screw driving instruments. Furthermore, bone screws used, for example, in maxillofacial applications are typically small and may be difficult to manipulate during installation. Thus, there is a concern in using such small screws in that they may be lost during surgery or may fall into the surgical site. The present invention allows a surgeon to simultaneously drill a screw hole and install a bone screw using a single device. In addition, the present invention allows a surgeon to preload multiple screws onto a screwdriver so that he can quickly manipulate and install multiple screws without removing the screwdriver from the incision area. The preloading of the screws is especially advantageous with the small bone screws used in maxillofacial surgery because it eliminates the need for the surgeon to manipulate multiple small screws on an individual basis, thus reducing the amount of user attention required to interface the screws with the instrument. The screw installation procedure may therefore be performed faster and safer, benefiting both surgeon and patient.

For certain applications, such as when the cannulated screws will be driven into the sternum, a single size or length of screw may not be used universally for all patients because the thickness of the sternum may vary significantly between patients. Thus, the surgeon may select a longer screw for a patient having a thick sternum, and a shorter screw for a patient having a relatively thinner sternum. Regardless of the length or size of the screw, however, it may be desirable that the drilling tip of the installation tool protrude from the end of the screw by the same distance. Thus, there is a need to provide a cannulated screw installation tool that can accept cannulated screws of different sizes and lengths, while maintaining a drilling tip that protrudes from the each screw by the same amount.

SUMMARY

An adjustable orthopedic tool is provided comprising a shaft portion with first and second ends and a longitudinal axis. The tool may have an adjustment portion and a fastener receiving portion. The first end may comprise a cutting portion configured to drill a hole in bone, and the second end may be configured to be coupled to a source of rotational motion. The tool may further have a fastener engaging portion and an adjustment mechanism mounted on the shaft and configured to allow the user to vary a distance between the cutting portion and the fastener engaging portion. The fastener receiving portion may be configured to receive at least a portion of a cannulated fastener thereon. The fastener engaging portion may also be configured to rotationally couple the tool to a driving portion of the cannulated fastener to transmit rotational motion thereto. The adjustment mechanism may be selectively movable along the longitudinal axis of the shaft to allow the tool to accept fasteners having different lengths.

The tool may be configured so that the cutting portion and the fastener engaging portion may be rotated at different speeds with respect to one another.

The adjustment portion of the shaft may comprise external threads and the adjustment mechanism may further comprise internal threads, and the threads may be engageable to allow the shaft and mechanism to be moved axially along a longitudinal axis of the shaft by rotating the pieces with respect to each other. Movement of the adjustment mechanism may adjust the distance between the fastener engaging portion of the adjustment mechanism and the cutting portion of the shaft.

The adjustment mechanism may further comprise at least first and second sleeves, the first sleeve comprising inner threads configured to engage the external threads of the shaft and the fastener engaging portion disposed on the second sleeve. The shaft may further comprise a plurality of calibration marks disposed between the adjustment portion and the second end, where each calibration mark corresponds to a predetermined distance between the fastener engaging portion of the adjustment mechanism and the first end of the shaft.

The first sleeve may further have a proximal end, wherein adjusting the adjustment mechanism so that the proximal end of the first sleeve lies adjacent to one of the calibration marks results in the fastener engaging portion of the adjustment mechanism being located a predetermined distance from the first end of the shaft corresponding to the mark. When a cannulated fastener having a head portion and a tip portion is received on the shaft, the distance may be adjustable to allow the fastener engaging portion of the adjustment assembly to rotationally engage the fastener head while allowing at least a first length of the shaft cutting portion to extend distally beyond the fastener tip.

The first length may be in the range of from about 0 millimeters (mm) to about 10 mm, and in one embodiment, the first length is about 1 mm. In another embodiment the first length is about 4.5 mm.

A bone fastener system is also provided. The system may comprise at least first and second cannulated fasteners, at least one adjustable tool having first and second ends and an adjustment portion, the first end comprising a cutting blade configured to drill hole in bone and a shaft portion configured to be received within the cannulation of the at least one cannulated screw; and at least one bone plate having at least one hole configured to receive the fastener to fix the plate the bone. The second end of the adjustable tool may be configured to be coupled to a source of rotational motion, and the tool may further have an intermediate shaft portion disposed between the first and second ends, the adjustment portion configured to be axially movable along the intermediate portion.

The adjustment portion may further comprise a distal end configured to rotationally engage a head portion of at least one of the first and second fasteners. The adjustment portion may further be configured to allow a user to vary a distance between the cutting blade and the distal end of the adjustment mechanism. The tool may be arranged so that the cutting blade and the adjustment portion distal end can be rotated at different speeds with respect to each other. The adjustment portion may further be configured to be selectively adjustable along the intermediate shaft portion to adjust an axial distance between the distal end of the adjustment portion and the tool first end. The intermediate shaft portion may comprise a plurality of calibration markings and the adjustment portion may have a proximal end, wherein when the adjustment portion is adjusted to align the proximal end adjacent to one of the plurality of markings results in the distal end of the adjustment portion may be located a predetermined distance from the tool first end.

The first fastener may have a head portion, a first length and a distal tip, wherein when the tool adjustment portion is adjusted to align the proximal end adjacent to one of the plurality of markings, the first end of the tool may be located a first predetermined distance distal to the first fastener distal tip. The first predetermined distance may be in the range of from about 0 mm to about 10 mm, and in one embodiment the first predetermined distance may be about 1 mm. Alternatively, the first predetermined distance may be about 4.5 mm.

The second fastener may have a head portion, a second length and a distal tip, wherein when the tool adjustment portion is adjusted to align the proximal end adjacent to one of the plurality of markings, the first end of the tool may be located a second predetermined distance distal to the second fastener distal tip. The first and second lengths may be substantially unequal, while the first and second predetermined distances may be substantially equal.

At least the first fastener may have a cannulation comprising a length, the cannulation having a polygonal shape for at least a portion of its length. At least the first fastener may have a head portion, the head portion comprising a flange having an underside configured to engage a bone or bone plate surface. The first fastener member may have at least one cutting flute for engaging and cutting bone. The fastener member may comprise self-tapping threads.

The intermediate portion of the tool may further comprising a first length, the first and second fasteners each comprising a second length, the first length being sufficient to allow at least the first and second fastener members to be simultaneously received on the intermediate portion. The first end of the tool may further comprise a raised portion for provisionally axially retaining at least one of the fastener members to the tool.

A method of installing at least a first bone fastener in bone is also provided. The fastener may comprise a cannulated bone fastener having a head portion and a tip portion, where at least a portion of the cannulation formed in a polygonal shape. The method may comprise: (a) providing a tool with first and second ends, a shaft having a drilling tip and an outer surface configured to receive the cannulation of the fastener, a sleeve having a distal end shaped to engage the polygonal portion of the cannulation of the fastener, and an adjustment mechanism for adjusting the distance between the drilling tip and the distal end of the sleeve; (b) inserting the first fastener onto the outer surface of the shaft; (c) engaging the sleeve with the polygonal portion of the fastener cannulation; (d) adjusting the distance between the drilling tip and the distal end of the sleeve to allow at least a portion of the cutting tip to extend distally beyond the fastener tip; (e) rotating the drilling blade of the screwdriver against the surface of a bone; (f) continuing rotation of the drilling blade until the screw is fully engaged in the bone; and (g) removing the screwdriver from the cannulation of the screw.

The fastener may have a head portion comprising a flange having an underside configured to engage a bone or bone plate surface. The fastener may also have at least one cutting flute for engaging and cutting bone. The tool shaft may have a proximal portion opposite the drilling tip, the distal portion comprising a plurality of calibrated markings, wherein step (d) further comprising aligning a proximal portion of the adjustment mechanism to align with at least one of the calibrated markings so that the cutting tip extends beyond the fastener distal tip by a corresponding pre-set amount.

The pre-set amount may be adjustable in the range of from about 0 mm to about 10 mm. The tool may have a retention feature to provisionally axially retain the fastener on the tool. The retention feature may comprise a flared portion adjacent the distal end of the tool sleeve, the flared portion configured to interfere with the polygonal portion of the fastener cannulation. A second cannulated fastener may further be provided, wherein the outer surface of the tool may be configured to receive the first and second cannulated fasteners at the same time.

BRIEF DESCRIPTION OF THE DRAWINGS

FIG. 1 is a side view of an exemplary embodiment of the tool of the present invention;

FIG. 2 is a side cutaway view of the tool of FIG. 1;

FIG. 3 is a side view of a shaft portion of the tool of FIG. 1;

FIG. 4 is a top view of the shaft portion of FIG. 3;

DETAILED DESCRIPTION OF ILLUSTRATIVE EMBODIMENTS

Figure 10A:
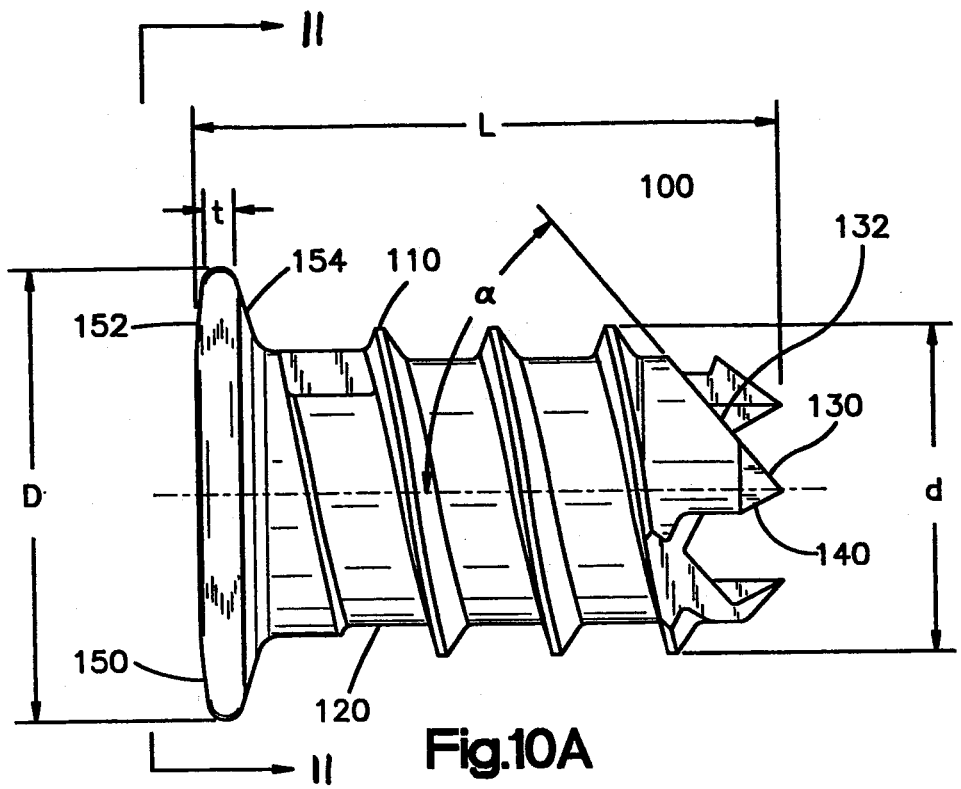
FIGS. 10A and 10B are side and end views, respectively, of an exemplary cannulated fastener for use with the tool of FIG. 1.
Figure 10B:
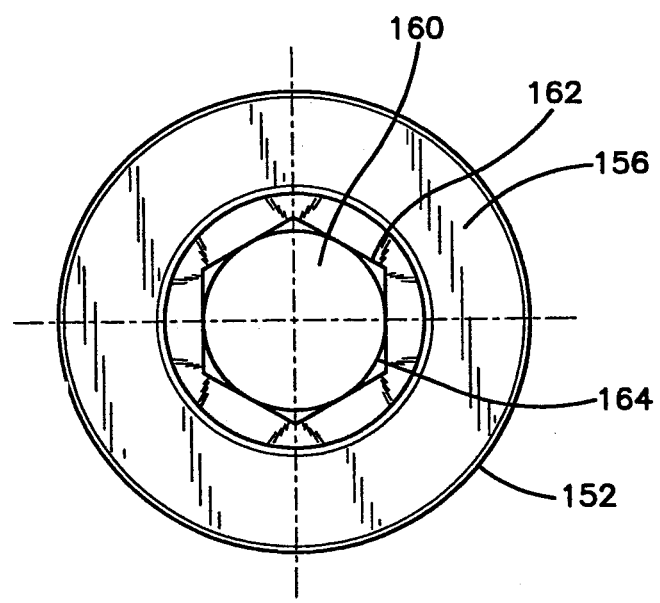

FIGS. 1 and 2 show an exemplary embodiment of an adjustable tool 1 for use in drilling a hole in bone and for driving any of a variety of cannulated fasteners into the drilled hole. The tool may have a distal drilling end 2, a proximal coupling end 3 and an adjustment portion 4. The drilling end 2 may be configured to drill a hole in a targeted bone segment, while the coupling end 3 may be configured for easy attachment to a source of rotational motion for powering the drilling end 2. The adjustment portion 4 may be configured to allow the tool 1 to accept a variety of different sized cannulated fasteners for insertion into the hole drilled by the drilling end 2 of the tool 1. In one embodiment, the fastener is a bone screw 100 (FIGS. 10a, 10b). It is noted, however, that while the tool 1 will generally be described for use with a cannulated bone screw, the invention may be used with any of a variety of different types of fasteners, a non-limiting listing of such fasteners including bone screws of the self-tapping and self-drilling variety, bone tacks, rivets, etc. Further, while the tool 1 may be described for use in particular applications (e.g. maxillofacial, cranial, mandible, etc), the invention may be applied to any area of the body in which it is advantageous to drive a cannulated fastener into bone.

One advantage of the present invention is that it allows the surgeon to use a single tool both to drill and to drive cannulated fasteners of different lengths into targeted bone segments. Such flexibility is important because the bony anatomy can vary significantly between patients (and even within a single bone in the same patient), and thus it may be important to provide the surgeon with a wide range of available screw lengths so that a specific screw size may be chosen which suits the individual patient's anatomy. Thus, providing fasteners in a variety of lengths gives the surgeon maximum flexibility in selecting the proper fastener for the application. Providing a single drilling and driving tool that may be used to drill and drive these various fasteners reduces the complexity of the operation and may reduce the overall time required to install the fasteners in the patient.

As will be described in greater detail below, the tool 1 may be adjustable so that it may be used to drill holes in bone and install fasteners of different sizes in the drilled holes. Thus, tool 1 may have a shaft portion 200 and an adjustment assembly 300. The shaft portion 200 may be configured to slidably receive a cannulated fastener 100 (FIGS. 10A, 10B) and may also have a drilling tip 220 configured to drill a hole into a targeted bone segment. The adjustment assembly 300 may comprise a fastener driving portion 330 configured to rotationally engage the fastener 100 to drive the fastener into the bone hole created by the drilling tip 220. The adjustment portion 300 may be used to adjust the distance between the drilling tip 220 and the fastener driving portion 330 to allow tool 1 to accept fasteners 100 of different lengths.

In use, a cannulated fastener 100 is loaded onto the tool 1 so that a proximal portion of the fastener 100 engages the fastener driving portion 330 of the tool 1. The adjustment assembly 300 may then be used to adjust the distance between the drilling tip 220 and the fastener driving portion 330 to suit the size of the fastener 100. The proximal end 3 of the tool 1 may then be connected to a source of rotational motion (e.g. air or electric powered, or hand powered), and the drilling tip 220 of the tool 1 may be engaged with the bone to form the desired hole. As the tool 1 is rotated and axial pressure is applied, the drilling tip 220 bores into the bone surface. The cutting flutes 140 of the fastener 100 may begin to cut into the bone when the drilling tip 220 reaches a certain depth. The tool 1 may then be further rotated until the fastener 100 is fully seated in the bone.

Figure 5:
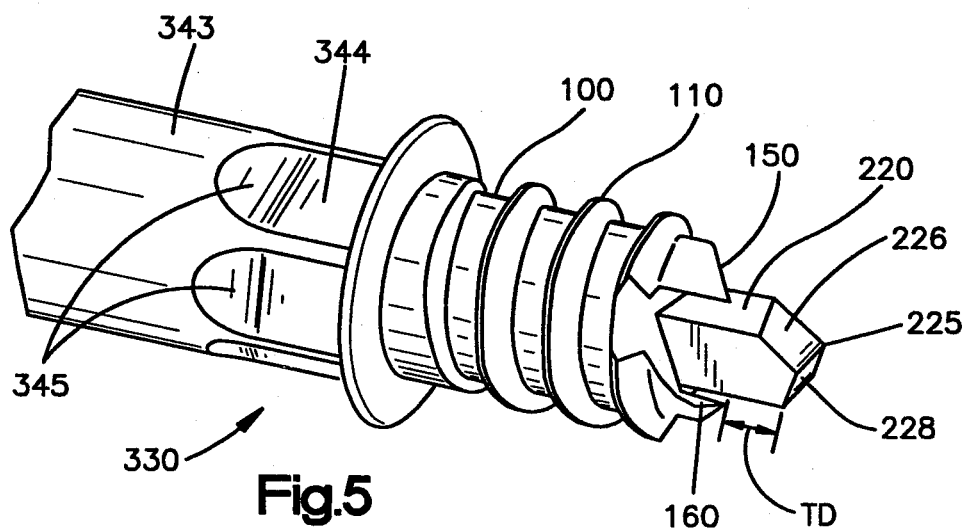
FIG. 5 is a perspective view of end portion of the tool of FIG. 1 engaged with an exemplary cannulated fastener.

To ensure proper formation of the bone hole, the tool may be adjusted to ensure that the drilling tip 220 extends past the tip 130 of the loaded fastener 100 by a predetermined amount "TD," (FIG. 5). This may ensure that the drilling tip 220 has a sufficient uncovered length to allow the hole to be sufficiently formed prior to contact with the cutting flutes 140 of the screw 100. It also may ensure that the drilling tip 220 does not protrude too far beyond the tip 130 of the loaded fastener 100, since excess protrusion could cause too deep a hole to be drilled (i.e. the hole may be significantly deeper than is required to fully seat the screw). Limiting the potential overprotrusion of the drilling tip 220 may be of particular importance in applications in which vital organs directly underlie the bone to be drilled (e.g. the heart or brain).

Figure 6A:
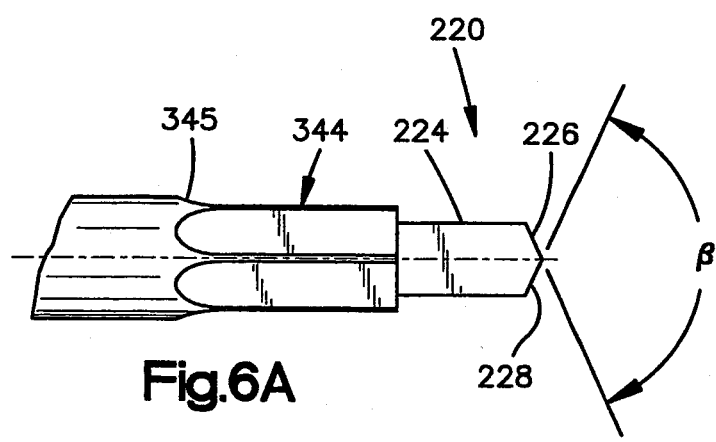
FIGS. 6A, 6B and 6C are detail side, reverse perspective and end views, respectively, of a cutting tip of the shaft portion of FIG. 3.
Figure 6B:
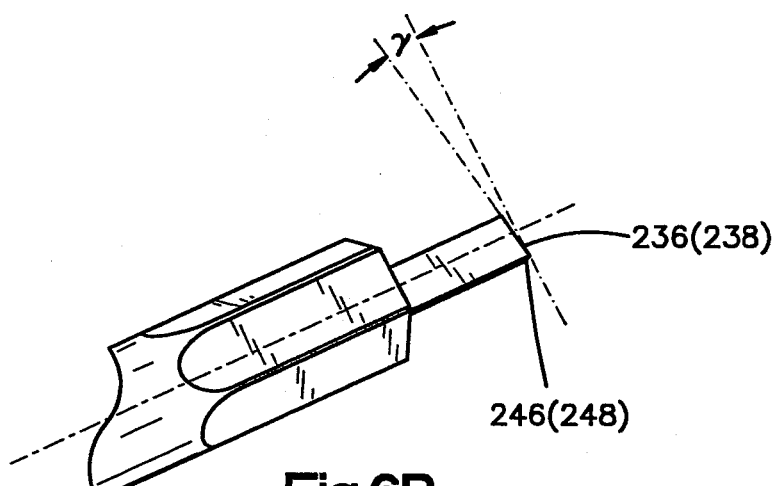
Figure 6C:
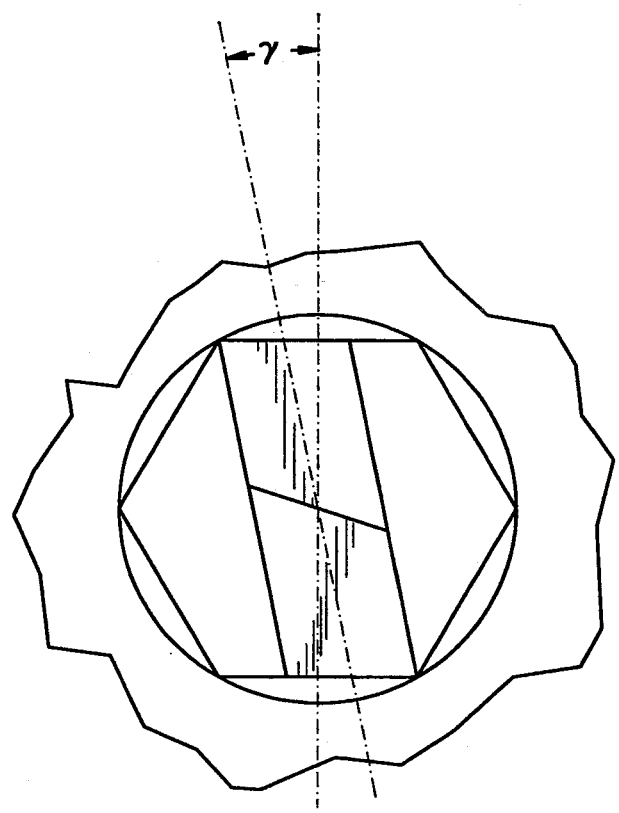

Referring again to FIG. 1, the shaft portion 200 may have a proximal coupling end 240, a distal drilling tip 220 configured for drilling into bone, and a threaded central portion 250 configured to engage the adjustment portion 300. The coupling end may comprise a male hex section 242 configured to rotationally engage a hex driver or other source of rotational motion. The coupling end may also comprise a circumferential radial groove configured to engage a detent mechanism (e.g. a ball detent) of the driver to provisionally retain the driver to the tool 1. As shown in greater detail in FIGS. 6A through 6C, distal drilling tip 220 may be flat with a pointed end 225 to facilitate cutting into bone. In the illustrated embodiment, drilling tip 224 has two opposed blade portions 226, 228 having cutting surfaces that, when viewed from the side, form an included angle $\beta$. Included angle $\beta$ may be selected in the range of from about 90° to about 160°. In an exemplary embodiment, $\beta$ is approximately 130°. Blade portions 226, 228 also may have faces 236, 238 that, when viewed from the top (as shown in FIGS. 6B and 6C), may be inclined at an angle $\gamma$ with respect to leading edges 246, 248. In one embodiment, $\gamma$ may be selected in the range of from about 5° to about 30°. In an exemplary embodiment, angle $\gamma$ may be approximately 10°. Drilling tips also may be provided having angles $\beta$ and $\gamma$ different from those identified herein, as will be apparent to one of ordinary skill in the art. It is also noted that any appropriate drilling tip design known in the art may be used to provide the desired cutting into bone.

In an alternative embodiment, the shaft 200 may be provided without a drilling tip 220, and the distal end 2 of the tool 1 may not extend past the tip 130 of the fastener 100 when the fastener is fit onto the tool 1. In such a case, a pilot hole may be drilled into bone using traditional methods (e.g., awl, tap, etc.), and the tool 1 with cannulated fastener 100 may be used to drive the fastener into the bone. Such a configuration may be advantageous when large sized fastener are used.

Threaded central portion 250 of shaft 200 may comprise a single, double or triple threaded section configured to threadably engage the inner threads of the proximal adjusting sleeve 320, to allow the position of the shaft 200 to be axially adjusted with respect to the adjustment assembly 300. The central portion 250 may comprise a pair of diametrically opposed flat sections 252, 254 configured to mate with corresponding flats 357, 359 provided in the adjustment assembly 300, as will be described in more detail later.

Between the threaded central portion 250 and the drilling tip 220 lies a reduced diameter portion 270 which sized to slidably receive both the distal sleeve portion 343 of the distal adjusting sleeve 340, and the cylindrical portion 164 of the fastener cannulation 160. This reduced diameter portion 270 also may provide for greater visibility of the surgical work site by reducing the transverse dimension of the portion of the tool 1 located between the drilling tip 220 and the threaded central portion 250.

Adjustment markings 260 may be provided on the shaft between the threaded central portion 250 and the coupling end 240. These markings 260 may be calibrated to allow the surgeon to quickly and easily adjust the tool 1 to the proper setting for each individual fastener. For example, where a 6.0 mm fastener is used, the surgeon may rotate the adjustment assembly 300 until the proximal end 326 of the proximal adjusting sleeve 320 lies adjacent the marking corresponding to the number "6." In this manner, the tool 1 can be adjusted so that the drilling tip 220 extends from the end of the fastener tip 130 by a predetermined amount "TD," (FIG. 5). Similar markings may be provided on the shaft 200 for all of the various lengths of screws that may be accommodated by the particular shaft 200. In the illustrated embodiment, screws having lengths up to and including 25 mm may be accommodated by shaft 200. In other embodiments, longer screws may be accommodated.

As shown in more detail in FIGS. 7A through 9C, the adjustment assembly 300 may comprise proximal and distal adjusting sleeves 320, 340 and an internal adjusting collar 350. When assembled, the adjustment assembly 300 threadably engages the shaft 200 to allow the position of the two elements 300, 200 to be axially adjusted simply by rotating the elements with respect to each other. Thus, a desired distance "td" (FIG. 5) between the drilling tip 220 of the shaft and the fastener driving portion 330 of the adjustment assembly 300 may be achieved. As previously noted, this adjustability ensures that fasteners of different lengths can all adequately engage the fastener driving portion 330, while maintaining a desired protrusion length "TD" of drilling tip 220 beyond tip 130 of the fastener 100. This desired protrusion "TD" will be preset so that a consistent protrusion is provided for a particular fastener length. This preset protrusion "TD" may be a value in the range of from about 0 mm to about 10 mm, and may depend upon the thickness of the plate that will be used with the fastener. Thus, in one embodiment for use in the sternum, the thickness of the plate may be about 3.5 mm, while the distance "TD" may be about 4.5 mm. Thus, the desired protrusion "TD" may be sufficient to allow the drilling tip 220 of the tool 1 to engage the bone before the fastener 100 engages the plate. Where the tool 1 is used in maxillofacial applications, the protrusion "TD" may be selected from the range of from about 0.8 mm to about 3 mm, and in one embodiment may be about 1 mm. In most applications, the protrusion "TD" will be such that the drilling tip 220 may drill slightly deeper into bone than is required to seat the associated fastener 100. Where the tool is used in neural applications (i.e. for drilling into the cranium), the protrusion "TD" may approach 0 mm to ensure that the drilling tip 220 does not breach the inner bone wall or contact the dura mater.

Figure 7A:
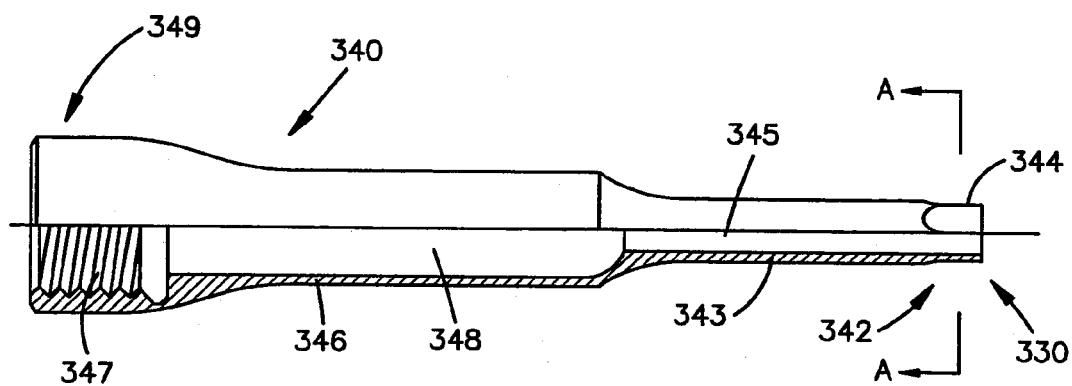
FIGS. 7A and 7B are side and end views, respectively, of a distal sleeve portion of the tool of FIG. 1.
Figure 7B:
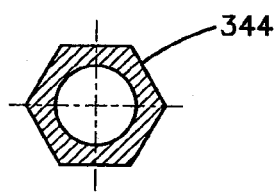

Referring to FIGS. 7A and 7B, the fastener driving portion 330 of the distal sleeve 340 may have a distal end 342 comprising an external hex 344 configured to engage portion of internal hex portion 162 of cannulation 160 of the cannulated fastener 100 (FIGS. 10A, 10B). The distal adjusting sleeve 340 may further have a distal sleeve portion 343, having a bore 345 sized to slidingly accept the reduced diameter distal portion 270 of shaft 200. Adjacent to the distal sleeve portion 343, central sleeve portion 346 may have a bore 348 sized to be slightly larger than the central threaded portion 250 of shaft 200. Thus, the shaft 200 may be translated proximally or distally within the adjustment assembly 300 without interfering with the any surface of the distal adjusting sleeve 320. The distal adjusting sleeve 320 may further have a proximal threaded end 347 configured to threadably engage the external threads 352 of the adjusting collar 350.

Figure 8A:
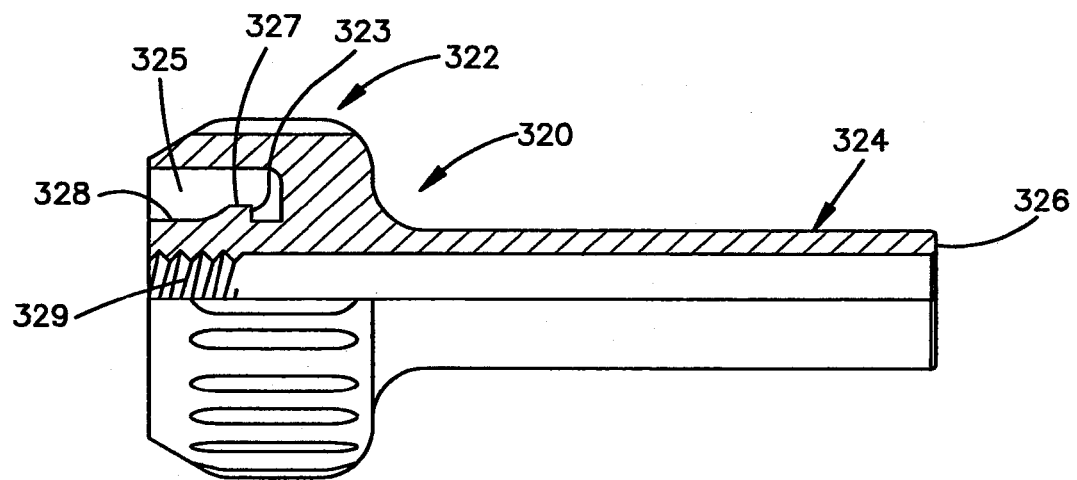
FIGS. 8A and 8B are side and end views, respectively, of a proximal sleeve portion of the tool of FIG. 1.
Figure 8B:
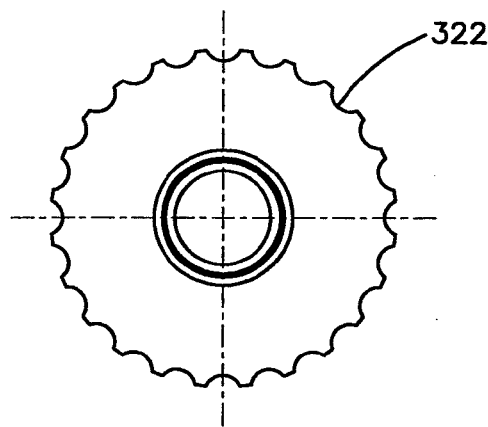

FIGS. 8A and 8B show the proximal adjusting sleeve 320 as having a proximal sleeve portion 324 with a proximal end 326, a central adjusting nut 322, and a distal portion 328 having internal threads 329 configured to threadably engage the central threaded portion 250 of shaft 200. The distal portion 328 may also comprise an annular recess 325 configured to receive the resilient finger elements 353 of the adjusting collar 350 (FIG. 9B). Thus, the distal portion 328 may also have a raised rim portion 327 internal to the annular recess 325. The raised rim portion 327 may further have a reverse shoulder 323 configured to engage and retain corresponding shoulders 355 of resilient fingers 353 of the adjusting collar 350 (to be discussed next).

Figure 9A:
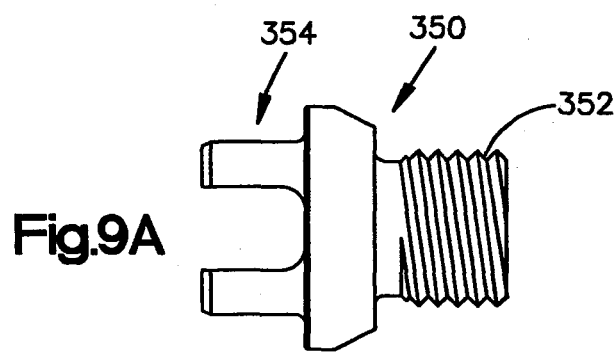
FIGS. 9A through 9C are side, detail cross-section, and end views, respectively, of an adjustment collar of the tool of FIG. 1.
Figure 9B:
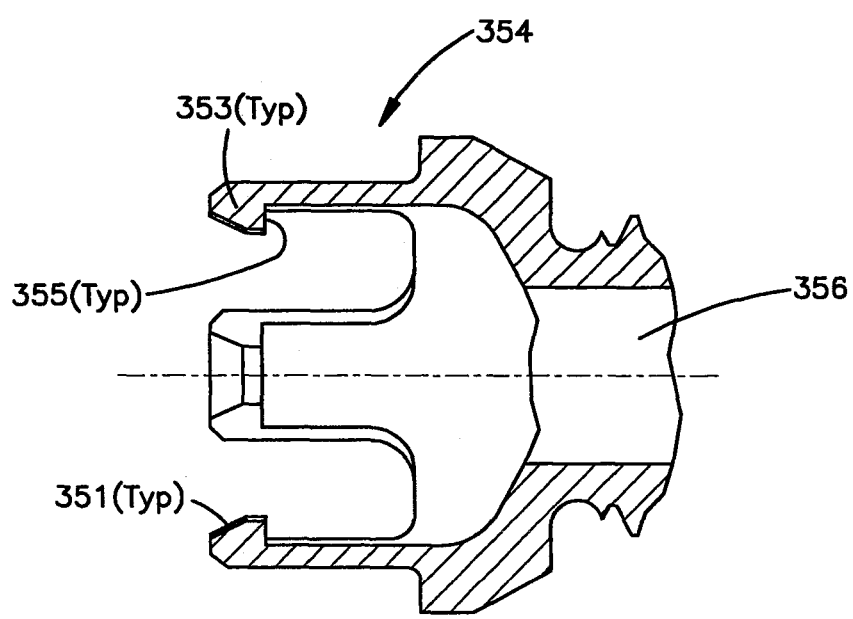
Figure 9C:
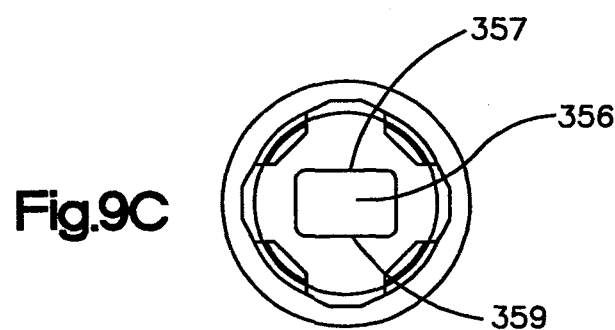

As shown in FIGS. 9A through 9C, the adjusting collar 350 may have a proximal sleeve engaging portion 354 and a distal sleeve engaging portion 352. As described above in relation to the proximal adjusting sleeve 320, the proximal sleeve engaging portion 354 may comprise a plurality of resilient finger elements 353, where each finger element has an sliding engaging surface 351 and a retention shoulder 355. The sliding engaging surface 351 may be sloped to provide a gentle expansion or flexion of the associated resilient finger 353 when the surface 351 is pressed against the raised rim portion 327 of the proximal adjusting sleeve 320. Thus, when the proximal sleeve engaging portion 354 is aligned with the annular recess 325 of the proximal sleeve 320 and the two pieces are pressed together, the engaging surfaces 351 of the resilient fingers 353 may contact the raised rim 327 of the sleeve 320 to deflect the fingers radially outward. As the pieces 350, 320 are pressed further together the fingers 353 may continue to deflect until they clear the rim portion 327. At this point, the fingers 353 may then snap back into their original unflexed position on the opposite side of the rim 327, thereby engaging shoulders 323, 355. Subsequent disassembly of the two pieces 320, 250 is prevented by the engagement of these shoulders. Thus, the proximal adjusting sleeve 320 and the adjustment collar 350 are axially locked but are free to rotate with respect to each other while the device is being adjusted.

The adjusting collar 350 may further comprise an axial opening 356 having parallel opposed flat sides 357, 359 configured to slidably receive the flat portion 252, 254 of the central threaded portion 250 of shaft 200. This arrangement allows the shaft 200 and the collar 350 to be freely axially movable with respect to each other, but rotationally fixes the two together. Thus, when the shaft 200 rotates during the drilling and driving operation, the adjusting collar 350 may rotate along with the shaft 200.

To assemble the device, the proximal end of the adjustment collar 350 is aligned with the distal end 324 of the proximal adjusting sleeve 320, and the two pieces are snapped together, as previously described. The proximal end of the distal adjusting sleeve 349 is then aligned with the distal end of the adjustment collar 350 and the two pieces are threaded together. The drilling tip 220 of shaft 200 is then inserted into the proximal sleeve portion 324 of the proximal adjusting sleeve 320 and shaft 200 is fully inserted into the adjustment assembly 300 the device until the internal threads 329 of the proximal adjustment sleeve 320 engage the central threaded portion 250 of the shaft 200. During this step, care must be taken to ensure that the flats 252, 254 on the shaft 200 are aligned with the flats 357, 359 of the adjustment collar 350.

Once the tool 1 has been assembled, the adjusting assembly 300 may be employed to adjust the relative axial positions of the shaft 200 and the adjustment assembly 300 thus allowing the tool 1 to accept a desired fastener 100. To adjust the tool 1, the central adjusting nut 322 may be rotated while holding the shaft 200 fixed. The relative rotation of the two pieces 322, 200 causes the corresponding threaded sections 329, 250 to translate the adjustment assembly 300 along the shaft (or vice versa), thereby modifying the distance "td" (FIG. 1) between the drilling tip 220 of the shaft 200 and the external hex 344 of the distal adjusting sleeve 340. To adjust the tool to receive a particular screw, the adjustment assembly 300 may be translated along the shaft 200 until the proximal sleeve end 326 of the adjusting assembly 300 lies immediately adjacent the desired measured marking 260 on the shaft 200 corresponding to the appropriate screw size. The screw 100 may then be positioned on the tool 1 and the drilling tip 220 may be applied to the bone to drill the hole in anticipation of the fastener. During drilling, the adjustment assembly 300 rotates together with shaft 200 due to the rotational locking interaction between the flats of the adjustment collar 350 and the shaft 200.

In an alternative embodiment, the tool 1 may be configured so that the adjustment assembly 300 rotates at less than the speed of the shaft 200. Such an arrangement may be advantageous where fasteners 100 are to be installed in particularly hard bone, since the drilling tip 220 may more easily cut into such hard bone if it is operating at a higher rate of speed (e.g. 2:1 or 3:1) compared with the tool 1 of FIG. 1. Such higher speeds, however, may not be appropriate for screwing the fastener 100 into the bone and/or plate. Thus, a dual-speed tool may be provided that will allow a single source of rotation, input via shaft coupling end 240, to rotate the drilling tip 220 at a first speed and the external hex 344 at a second speed. To implement such a design, the locking interaction between the flats of the adjustment collar 350 and the shaft 200 may be eliminated, and a transmission assembly (e.g. a planetary gear or similar assembly) may be provided between the shaft 200 and the adjustment assembly 300 to step-down the rotational speed input via the shaft coupling end 240. Such an arrangement may allow the shaft 200 and drilling tip 220 to operate at a desirably high speed, while allowing the external hex 344 of the distal sleeve 340 to operate at an optimal (slower) speed for screwing the fastener 100 into the bone/plate. It is noted that such a geared design conversely could be implemented to allow the adjustment assembly 300 to rotate faster than the shaft 200.

Referring once again to FIGS. 1 and 2, the threaded engagement between the shaft 200 and the adjustment assembly 300 allows the shaft 200 to be readily replaced. This may be advantageous where, for example, a drilling tip 220 becomes dulled. The shaft 200 with the dulled tip 220 may be replaced with a new shaft 220 having a sharp tip 220. Alternatively, where fasteners having different cannulation diameters or dimensions are provided, an additional shaft or shafts may be provided to accommodate such alternative cannulation sizes.

In one embodiment, a variety of the fasteners 100 may be provided for use with the tool 1 for a particular application (e.g. maxillofacial, sternal, neural, mandible), The fasteners 100 may be provided in various different lengths to accommodate different bone thicknesses. Regardless of length, however, the fasteners may all be provided with the same size cannulation 160 so that a single tool 1 may be used to install all of the fasteners.

In an alternative embodiment, an additional shaft 1200 may be provided for use with the tool, where the additional shaft 1200 is sized and configured to accept fasteners 100 having larger or smaller cannulation dimensions compared to those accepted by the first shaft 200. Thus, in one application, the additional shaft 1200 may be longer and may have a larger reduced-diameter portion 1270 than the reduced-diameter portion 270 of shaft 200. Such an additional shaft 1200 may be provided for applications in which a large range of fastener lengths and/or diameters is desired due to wide variations in the dimensions of the bony anatomy between patients. Thus, in one application (e.g. for use in the sternum) a pair of shafts 200, 1200 may be provided. The first shaft 200 may be sized and configured to accept fasteners having lengths from about 6 mm to about 18 mm, while the second shaft 1200 may accept fasteners having lengths from about 18 mm to about 24 mm. Further, while the additional shaft 1200 has been described for use with larger fasteners, it will be apparent to one of skill in the art that the shaft 1200 may also be sized and configured to be shorter and have a smaller reduced-diameter portion than the reduced-diameter portion 270 of shaft 200 to accept smaller fasteners than those for use with shaft 200.

In a further embodiment, a "low-profile" shaft 200 may be provided in which the reduced-diameter portion 270 is of a very small diameter in order to increase visibility in the surgical work area. In one embodiment of a "low-profile" shaft 200, the reduced-diameter portion 270 may have a diameter of about 1.5 mm.

FIGS. 10A and 10B show an exemplary embodiment of a cannulated bone screw 100 for use with the tool of FIG. 1 Bone screws of this type may be used in a variety of orthopedic applications, such as to attach bone plates to opposing bone segments to hold the bone segments in a desired relative position during healing. When used in locations in the body in which little fat or tissue lies between the bone and skin, the bone plates and screws may be designed to have a "low profile" to minimize any aesthetic impact on the patient's appearance during the healing process.

Bone screw 100 may comprise threads 110 on the outer diameter of the shaft 120, a tip 130, and a head region 150. Tip 130 may have one or more cutting flutes 140 suitable for cutting into bone. Head region 150 may further comprise a flange 152 for seating the screw 100 on a bone or bone plate surface. The flange 152 may have an upper side surface 156 and an underside surface 154. The upper side surface 156 may be substantially flat, forming a plane substantially perpendicular to the longitudinal axis of the shaft 120. The underside surface 154 of flange 152 may likewise be substantially flat (i.e., parallel to the plane of the upper side surface 156) or it may be sloped toward the shaft so as to be non-orthogonal with respect to the screw shaft axis and non-parallel to the plane of the upper side surface 156. Alternatively, the underside surface 154 may be spherically shaped so as to conform to spherical bone screw holes formed in an associated bone plate. In one embodiment, the thickness "t" may be from about 0.2 millimeters (mm) to about 6.0 mm. For the embodiment of the screw having a sloped underside surface 154, the head flange 152 thickness "t" may vary (i.e., it may be thinner near the outer circumference of the flange and thicker near the shaft 120). In addition, screw 100 may have a locking head comprising a conical, cylindrical, or spherically threaded section.

Figure 11:
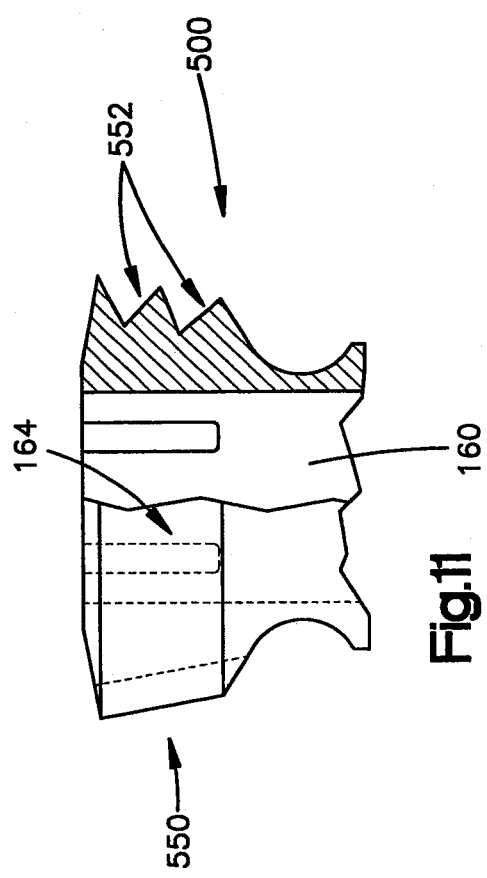
FIG. 11 is a side view of an alternative embodiment of a screw having a threaded head for use with the tool of FIG. 1.

FIG. 11 shows an alternative embodiment in which screw 500 may be used in conjunction with a bone plate having threaded bone screw holes. The screw of this embodiment may have a head region 550 comprising threads 552 configured to engage the threads disposed within the plate hole, to lock the screw 500 to the plate. In the illustrated embodiment, screw 500 has a locking head comprising conical threads 552 which are configured to mate with corresponding conical threads of a bone plate. The screw 500 of this embodiment may alternatively be provided with a spherical threaded head section, configured to engage a corresponding spherical threaded section of the bone plate. When screws having threaded head regions are provided, the pitch of such threads may match the pitch of the threads in the body of the screw, such that the rate of advancement of the engagement of the screw into the plate may be the same as the rate of advancement of the screw body into the bone.

Referring again to FIGS. 10A and 10B, a cannulation 160 may extend through the screw shaft 120 to allow the tool 1 to rotatably engage the cannulation and to transmit driving torque so that screw 100 may be driven into a bone. In the illustrated embodiment the cannulation 160 has two distinct portions. The first portion 162, located near the screw head region 150, has a hexagonal shape configured to engage the external hex 344 of the distal adjusting sleeve 340. The second portion 164 has a cylindrical shape configured to slidably receive the cylindrical reduced diameter portion 270 of the tool shaft 200 (FIGS. 4 &5). In an exemplary embodiment, the cannulation 160 has an axial length equal to the length "L" of the fastener 100. The first portion 162 of cannulation 160 has an axial length of at least 0.1 mm, with the remainder of the axial length of the cannulation 160 comprising cylindrically-shaped second portion 164.

The first portion 162 of the cannulation 160 may take any appropriate polygonal or non-polygonal shape. Likewise the first portion 162 may be provided with any of a variety of ridges, grooves, notches, etc., appropriate for engaging the corresponding surface features of driving portion 330 of the tool 1. The screw 100 may further comprise a length "L", which may be selected in the range of from about 2 mm to about 60 mm, an outside screw diameter "d," which may be selected in the range of from about 1.5 mm to about 5.0 mm, and a flange diameter "D," which may be selected in the range of from about 2.0 mm to about 6.0 mm.

Screw 100 may have a tip 130 with a plurality of cutting flutes 140, each flute 140 having a trailing edge 132 oriented at an angle α with respect to the longitudinal axis of the screw. In one embodiment, α may be selected in the range from about 35° to about 70°. In an exemplary embodiment, α may be approximately 50°. The advantage of selecting a trailing edge angle in the aforementioned range is that it permits a reasonably sized cutting flute without removing too much thread surface from the screw, which could reduce pullout strength of the screw from the bone. Threads 110 may have a pitch selected in the range of from about 0.15 mm to about 2.0 mm. In an alternative embodiment, thread height may be selected in the range of about 0.1 mm to about 0.75 mm. Screws having flute angles and geometries, thread pitches, and thread heights different from those identified herein may also be provided, as will be apparent to one of ordinary skill in the art.

Threads 110 may be self-tapping, and in an alternative embodiment, the screw 100 may also be self-drilling. The cannulated screws 100 may be made of any of a variety of materials, such as stainless steel, titanium, polymer, or bioresorbable materials. Furthermore, the invention is not limited to cannulated screws, but may include other appropriate cannulated bone fasteners such as bone tacks, rivets, etc. Where bone tacks, rivets or other bone fasteners are used they may likewise be provided in a variety of materials such as metals (e.g., stainless steel or titanium), polymer, or bioresorbable materials.

Head region 150 may have a thickness "t" that is very small, owing to the fact that most of the torque from the screwdriver may be transmitted to screw 100 via the cannulation in the shaft. This is different from typical bone fasteners in which the screwdriver engaging surface is located almost entirely within the head of the fastener, thus requiring a substantial head thickness to provide corresponding high strength. The cannulated shaft arrangement of the present invention eliminates the need for such a large head, and as a result, flange 152 of head region 150 may have a very low profile. Such a low profile fastener may be particularly advantageous in applications where there is little muscle or other tissue situated between the screw and/or bone plate and the patient's skin, such as the sternum, where bone plates are installed subcutaneously in a prominent region of the chest. Bone screws having normal head profiles may protrude significantly from the top of the associated bone plate, thus resulting in a visible bump or discontinuity in the skin. The thin head profile of screw 100, however, may protrude only slightly, or not at all, from the top surface of the bone plate, thus providing no significant additional discontinuity in the patient's features. Nevertheless, a low head profile is not critical to the success of the present invention, and screws having any head profile known in the art may be used in accordance with the desires of the installing surgeon.

Referring again to FIG. 5, screw 100 is installed on the distal end 2 of tool 1. The reduced diameter shaft portion 276 (hidden by screw) slidingly accepts the cylindrical portion 164 of cannulation 160, while the hexagonal portion 162 of the cannulation engages the external hex 344 of the distal adjusting sleeve 340. This enables the tool 1 and screw 100 to rotate together.

The tool 1 may also incorporate a provisional retention feature to keep the fastener 100 engaged with the tool 1 until the fastener is driven into bone. In one embodiment, external hex 344 may have a flared portion 345 which may interact with the head flange 152 and hexagonal portion 162 of cannulation 160 of screw 100. Thus, the cannulation 160 of screw 100 may wedge against the flared portion 345, causing an interference between the surfaces that may provisionally axially lock them together. This interference may be slight so that it will not interfere with the separation of the tool 1 and fastener 100 when the fastener is driven into bone.

Alternative embodiments of this retention feature may comprise a slight protrusion or raised ridge on the reduced diameter shaft portion 276 that may cause an interference with the inner surface of cannulation 160 similar to that described above in relation to the flared portion 345.

Figure 12:
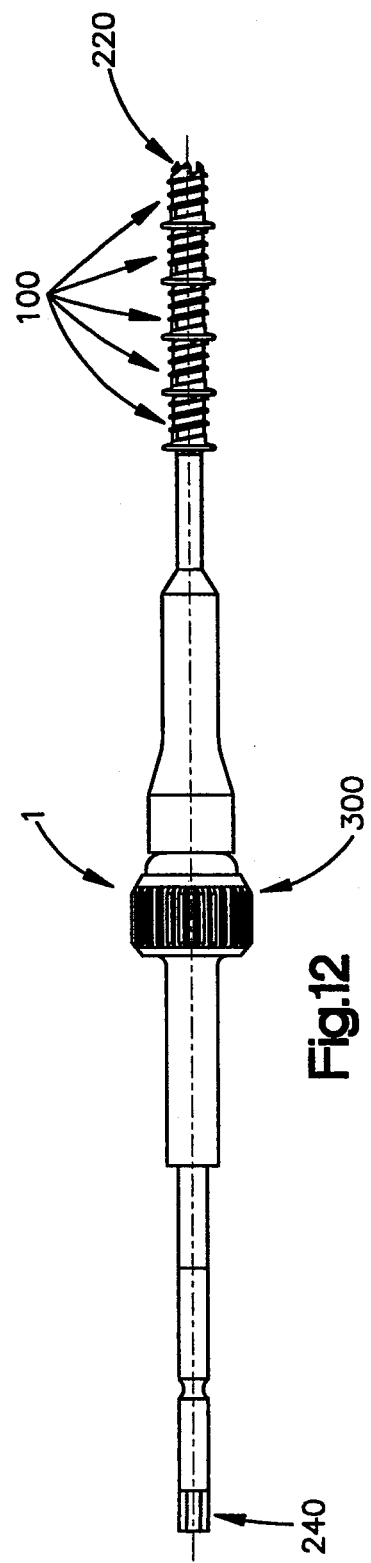
FIG. 12 is a side view of an alternative embodiment of the tool of the present invention having a multiple-fastener receiving feature.

An alternative embodiment of the tool 1 is illustrated in FIG. 12. In this embodiment, the tool 1 is sized to accept multiple stacked fasteners 100. As such, reduced diameter portion 270 of shaft 200 may be extended to allow the fasteners 100 to be accepted thereon. The adjustment assembly 300 of this embodiment may be initially adjusted to accommodate the fastener stack, and may be thereafter adjusted by a predetermined amount after each fastener is driven into the bone to ensure the drilling tip 220 protrudes by the prescribed amount beyond the distal tip 130 of the distal most fastener 100. This embodiment may be advantageous where multiple small fasteners are being used, as handling such small fasteners in the surgical environment can be difficult. The shaft 200 of this embodiment may also have one or more provisional locking features as described above in relation to the embodiment of FIG. 1, to ensure the fastener stack remains on the tool 1 until driven.

To use the tool 1, the surgeon may select a fastener 100 and slide it over the distal drilling end 2 of tool 1. The fastener 100 may be slid up the shaft 200 until the head region 150 engages the external hex portion 344 of the distal sleeve 340. The fastener 100 may be pressed into the hex portion 344 to provisionally axially lock the fastener to the tool 1. The surgeon may then adjust the tool 1 to achieve the desired protrusion "TD" of the drilling tip 220 beyond the fastener tip 130. This adjustment may be performed by grasping the shaft 200 and turning the adjusting nut 322 of the adjustment assembly 300 until the proximal end 326 lies adjacent the appropriate marking 260 on shaft 200. For example, if the tool 1 is being used to drill and drive a 6 mm screw, then the nut is turned appropriately so that the proximal end 326 lies adjacent the marking 260 numbered "6."

Once the screw 100 is fit to the tool 1, pointed end 225 of shaft 200, which extends distally beyond the end of the screw 100, may be applied to the surface of a targeted bone area and rotated. The rotation of blade portions 226, 228 against the bone along with the application of axial force, results in a cutting of the bone accompanied by an axial advance of tool 1 along with screw 100 into the bone. When the hole in the bone reaches a depth sufficient for the screw 100 to engage the bone, cutting flutes 150 of screw 100 may engage the bone surface and enlarge the diameter of the hole in the bone. Self-tapping threads 110 may then engage the bone and the bone screw 100 may continue to advance as the screw is rotated. It is noted that this advancement may continue irrespective of any further axial movement of the screwdriver, owing to the self-tapping nature of the threads which, when the screw is rotated, may cause the screw to drive itself down into the drilled hole. Thus, full seating of the screw in bone may be achieved by holding the screwdriver axially fixed as it rotates and allowing the screw to translate along the hex surface as it tunnels into the bone. When fastener 100 is driven into the bone to the desired depth, tool 1 can be removed by pulling it axially out and away from cannulation 160 of the fastener 100. Thereafter, another fastener may be applied to drilling tip 220 of the tool 1 for subsequent drilling and insertion. For the multiple-fastener tool, the adjustment assembly 300 may be re-adjusted after each fastener 100 is inserted to push the next distal-most fastener in the stack into position for insertion.

It should be noted that although the tool 1 has been described in relation to drilling and driving fasteners in maxillofacial, sternal, mandible and cranial bones, the invention is not limited to such particular applications, but may cover any appropriate screws or other fasteners used in any orthopedic applications. Thus, the tool and fasteners may have dimensions different than those specifically identified herein without departing from the inventive nature of the device.

A surgical kit, including at least one tool 1 as previously described and a plurality of cannulated fasteners 100 also as previously described, may be provided. At least one replacement shaft 200 may be also be provided with the kit. The replacement shaft 200 may be substantially identical to the shaft 200 provided assembled with the tool 1, or it may be configured to receive larger or smaller fasteners (in length and/or diameter) than the shaft 200 provided assembled with the tool 1. The plurality of cannulated fasteners 100 may have different lengths and outside diameters. A bone plate (not shown) may also be provided in the kit. For the multiple fastener tool, fasteners may be provided preloaded onto the tool shaft, or they may be provided separately. The tool 1 may be made of stainless steel, titanium, a suitable polymer, or other appropriate material known in the art. Portions of the tool 1 may be made of different materials. Likewise, the fasteners 100 and plate may be made of stainless steel, titanium, a suitable polymer, or other appropriate material known in the art. In one embodiment, at least one of the fasteners is made of a bioresorbable polymer. The bone plate may also be made of a bioresorbable polymer.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed:

1. A bone fastener system comprising:
   at least first and second fasteners, each of the fasteners defining a cannulation; and
   at least one tool that is elongate along a central axis including:
   a shaft having a first portion comprising a cutting blade configured to drill a hole in bone, and a second portion including external threads, wherein the shaft is configured to be at least partially received within the cannulation of the at least first and second fasteners; and
   an adjustment sleeve having an internal bore configured to receive the shaft, the adjustment sleeve having internal threads configured to engage the external threads of the shaft when the shaft is received within the adjustment sleeve, such that rotation of the adjustment sleeve relative to the shaft about the central axis translates the shaft relative to the adjustment sleeve along the central axis.

2. The bone fastener system of claim 1, wherein the shaft includes a third portion configured to be coupled to a source of rotational motion, and the second portion is disposed between the first and third portions.

3. The bone fastener system of claim 2, wherein the at least first and second fasteners each include a head portion and wherein the adjustment sleeve is a proximal adjustment sleeve, the tool further comprising a distal adjustment sleeve translationally coupled to the proximal adjustment sleeve, the distal adjustment sleeve having a distal end configured to engage the head portion of at least one of the at least first and second fasteners, such that rotation of the proximal adjustment sleeve relative to the shaft varies a distance between the cutting blade and the distal end of the distal adjustment sleeve.

4. The bone fastener system of claim 3, wherein the distance between the cutting blade and the distal end of the distal adjustment sleeve is sufficient to allow at least the first and second fasteners to be simultaneously received by the tool.

5. The bone fastener system of claim 3, wherein the shaft of the at least one tool further comprises:
   a fourth portion, located distally from the external threads of the second portion, the fourth portion configured to extend into the cannulation of each of the at least first and second fasteners.

6. The bone fastener system of claim 5, wherein the at least one tool further comprises:
   a collar having a proximal end and a distal end, the collar configured to rotatably connect to the proximal adjustment sleeve, the collar having an internal bore configured to receive the shaft.

7. The bone fastener system of claim 6, wherein the at least one tool further comprises:
   the distal adjustment sleeve having a proximal end opposite the distal end, the proximal end being connected to the collar, and the distal end having a fastener engaging portion, the distal adjustment sleeve having an internal bore configured to receive the shaft, wherein rotational movement of the shaft causes rotational movement of the fastener engaging portion of the distal adjustment sleeve.

8. The bone fastener system of claim 7, wherein rotating the proximal adjustment sleeve causes the fastener engagement portion of the distal adjustment sleeve to move along the central axis of the shaft to adjust a distance between the fastener engagement portion and the cutting blade.

9. The bone fastener system of claim 8, wherein the first portion of the shaft and the fastener engaging portion of the distal adjustment sleeve can be rotated at different speeds with respect to one another.

10. The bone fastener system of claim 8, wherein the internal bore of the collar has a flat surface configured to mate with a flat surface portion of the shaft.

11. The bone fastener system of claim 8, wherein the distal adjustment sleeve has external threads located proximate to its proximal end, and wherein the collar has internal threads located proximate to its distal end, and wherein the distal adjustment sleeve is threadedly connected to the collar.

12. The bone fastener system of claim 8, the shaft further comprising a plurality of calibration marks, each calibration mark corresponding to a predetermined distance between the cutting blade of the shaft and the tip portion of the first fastener.

13. The bone fastener system of claim 8, wherein the at least first and second fasteners each include a tip portion opposite the head portion, and wherein when the at least first and second fasteners are received on the fourth portion of the shaft and the fastener engaging portion of the distal adjustment sleeve is engaged with the head portion of the at least first and second fasteners, the proximal adjustment sleeve can be rotated to provide a first length between the cutting blade and the tip portion of the first fastener.

14. The bone fastener system of claim 13, wherein the first length is between 0 mm and 10 mm.

15. The bone fastener system of claim 14, wherein the first length is about 1 mm.

16. The bone fastener system of claim 14, wherein the first length is about 4.5 mm.

17. The bone fastener system of claim 3, wherein the cutting blade and the distal end of the distal adjustment sleeve can be rotated at different speeds with respect to each other.

18. The bone fastener system of claim 3, wherein the shaft includes a plurality of calibration markings and the proximal adjustment sleeve having a proximal end, wherein when the proximal end of the proximal adjustment sleeve is aligned with one of the plurality of markings, the distal end of the distal adjustment sleeve is located a predetermined distance from the cutting blade.

19. The bone fastener system of claim 18, the first fastener having a distal tip spaced from the head portion of the first fastener, wherein when the proximal end of the proximal adjustment sleeve is aligned with one of the plurality of markings, the cutting blade is located a first predetermined distance distal from the first fastener distal tip.

20. The bone fastener system of claim 19, wherein the first predetermined distance is in the range of from about 0 mm to about 10 mm.

21. The bone fastener system of claim 19, wherein the first predetermined distance is about 1 mm.

22. The bone fastener system of claim 19, wherein the first predetermined distance is about 4.5 mm.

23. The bone fastener system of claim 19, the second fastener having a distal tip spaced from the head portion of the second fastener, wherein when the proximal end of the proximal adjustment sleeve is aligned with one of the plurality of markings, the cutting blade is located a second predetermined distance distal from the second fastener distal tip.

24. The bone fastener system of claim 23, wherein the first fastener defines a first length measured from the head portion to the distal tip of the first fastener and the second fastener defines a second length measured from the head portion to the distal tip of the second fastener, and the first and second lengths are substantially unequal, and the first and second predetermined distances are substantially equal.

25. The bone fastener system of claim 1, wherein at least the first fastener has a cannulation comprising a length, the cannulation having a polygonal shape for at least a portion of its length.

26. The bone fastener system of claim 1, wherein at least the first fastener has a head portion, the head portion comprising a flange having an underside configured to engage a bone or bone plate surface.

27. The bone fastener system of claim 1, wherein the fastener member has at least one cutting flute configured to engage and cut bone.

28. The bone fastener system of claim 1, wherein the fastener member comprises self-tapping threads.

29. The bone fastener system of claim 1, wherein the tool further comprises a raised portion for provisionally axially retaining at least one of the first and second fasteners to the tool.

30. The bone fastener system of claim 1, further comprising at least one bone plate having at least one hole configured to receive at least one of the at least first and second fasteners to fix the bone plate to an underlying bone.

31. A bone fastener system comprising:
a fastener defining a cannulation; and
a tool that is elongate along a central axis, the tool including:
a shaft having a distal end and a proximal end spaced from the distal end, the distal end including a cutting blade configured to drill a hole in bone, and the proximal end configured to be coupled to a driving member, wherein the shaft is configured to receive the fastener such that the shaft passes at least partially through the cannulation; and
an adjustment sleeve having an internal bore configured to receive the shaft such that the adjustment sleeve is positioned between the distal end and the proximal end of the shaft;
wherein the adjustment sleeve is translatable relative to the shaft along the central axis, such that as the adjustment sleeve translates relative to the shaft in a first direction the adjustment sleeve moves closer to the distal end and farther from the proximal end.

32. The bone fastener system of claim 31, wherein the adjustment sleeve is translatable relative to the shaft along the central axis, such that as the adjustment sleeve translates relative to the shaft in a second direction the adjustment sleeve moves farther from the distal end and closer to the proximal end.

33. The bone fastener system of claim 31, wherein the adjustment sleeve is rotatable relative to the cutting blade about the central axis and the cutting blade is translatable relative to the adjustment sleeve along the central axis.

34. The bone fastener system of claim 31, wherein the fastener includes a head portion and wherein the adjustment sleeve is a proximal adjustment sleeve, the tool further comprising a distal adjustment sleeve translationally coupled to the proximal adjustment sleeve, the distal adjustment sleeve having a fastener driving portion configured to engage the head portion, such that rotation of the proximal adjustment sleeve relative to the shaft varies a distance between the cutting blade and the fastener driving portion.

35. The bone fastener system of claim 31, wherein the fastener is a first fastener defining a first cannulation, the system further comprising a second fastener defining a second cannulation, and wherein the shaft is configured to receive both the first and second fasteners simultaneously such that the shaft passes at least partially through both the first and second cannulations.

36. The bone fastener system of claim 35, further comprising at least one bone plate having at least one hole configured to receive at least one of the at least first and second fasteners to fix the bone plate to an underlying bone.

37. A bone fastener system comprising:
a fastener defining a cannulation; and
a tool that is elongate along a central axis, the tool including:
a shaft having a distal end and a proximal end spaced from the distal end, the distal end including a cutting blade configured to drill a hole in bone, and the proximal end configured to be coupled to a driving member, wherein the shaft is configured to receive the fastener such that the shaft passes at least partially through the cannulation; and an adjustment sleeve having an internal bore configured to receive the shaft such that the adjustment sleeve is positioned between the distal end and the proximal end of the shaft, the adjustment sleeve further comprising a fastener driving portion configured to be rotationally coupled to the fastener such that as the adjustment sleeve rotates relative to the shaft about the central axis, the fastener driving portion rotates relative to the shaft about the central axis.

38. The bone fastener system of claim 37, wherein as the adjustment sleeve rotates relative to the shaft about the central axis, the fastener driving portion translates relative to the cutting blade along the central axis.

39. The bone fastener system of claim 37, wherein the fastener is a first fastener defining a first cannulation, the system further comprising a second fastener defining a second cannulation, and wherein the shaft is configured to receive both the first and second fasteners simultaneously such that the shaft passes at least partially through both the first and second cannulations.

40. The bone fastener system of claim 39, further comprising at least one bone plate having at least one hole configured to receive at least one of the at least first and second fasteners to fix the bone plate to an underlying bone.

* * * * *